US012797367B2

(12) United States Patent
Lee et al.

(10) Patent No.: US 12,797,367 B2
(45) **Date of Patent: *Nov. 17, 2026**

(54) PHARMACEUTICAL COMPOSITION COMPRISING 1-(3-CYANO-1-ISOPROPYL-INDOL-5-YL)PYRAZOLE-4-CARBOXYLIC ACID

(71) Applicant: LG CHEM, LTD., Seoul (KR)

(72) Inventors: Jieun Lee, Seoul (KR); Heemin Gwak, Seoul (KR); Seong Hye Shin, Seoul (KR); Ji Young Min, Seoul (KR); Min Hee Kim, Seoul (KR); Junyu Kim, Seoul (KR); Jung Youn Seo, Seoul (KR); June Sik Mune, Seoul (KR)

(73) Assignee: LG CHEM, LTD., Seoul (KR)

( * ) Notice: Subject to any disclaimer, the term of this patent is extended or adjusted under 35 U.S.C. 154(b) by 396 days.

This patent is subject to a terminal disclaimer.

(21) Appl. No.: 18/569,571

(22) PCT Filed: Jun. 15, 2022

(86) PCT No.: PCT/KR2022/008450
§ 371 (c)(1),
(2) Date: Dec. 12, 2023

(87) PCT Pub. No.: WO2022/265382
PCT Pub. Date: Dec. 22, 2022

(65) Prior Publication Data

US 2024/0285583 A1 Aug. 29, 2024

(30) Foreign Application Priority Data

Jun. 15, 2021 (KR) ........................ 10-2021-0077709

(51) Int. Cl.
*A61K 31/4155* (2006.01)
*A61K 9/00* (2006.01)
(Continued)

(52) U.S. Cl.
CPC ........ *A61K 31/4155* (2013.01); *A61K 9/0053* (2013.01); *A61K 31/165* (2013.01);
(Continued)

(58) Field of Classification Search
CPC .............. A61K 31/4155; A61K 9/0053; A61K 31/165; A61K 45/06; A61P 19/02; A61P 19/06; A61P 13/12; A61P 9/04
(Continued)

(56) References Cited

U.S. PATENT DOCUMENTS

2009/0042887 A1 2/2009 Lademacher et al.
2010/0056521 A1 3/2010 Shimizu et al.
(Continued)

FOREIGN PATENT DOCUMENTS

CN 102574839 A 7/2012
CN 103459381 A 12/2013
(Continued)

OTHER PUBLICATIONS

Pillinger et al , Therapeutic approaches in the treatment of gout, Seminars in Arthritis and Rheumatism 50 ,2020, p. S24-S30. (Year: 2020).*
(Continued)

*Primary Examiner* — Taylor V Oh
(74) *Attorney, Agent, or Firm* — SALIWANCHIK, LLOYD & EISENSCHENK

(57) ABSTRACT

The present invention relates to a pharmaceutical composition comprising 1-(3-cyano-1-isopropyl-indol-5-yl)pyrazol-4-carboxylic acid or a pharmaceutically acceptable salt thereof, and a method of treating or inhibiting a hyperuricemia-related disease using the same, and the pharmaceutical composition of the present invention may effectively reduce the blood uric acid concentration in a patient with a hyperuricemia-related disease.

18 Claims, 3 Drawing Sheets

(51) Int. Cl.
*A61K 31/165* (2006.01)
*A61K 45/06* (2006.01)
*A61P 19/02* (2006.01)
*A61P 19/06* (2006.01)

(52) U.S. Cl.
CPC .............. *A61K 45/06* (2013.01); *A61P 19/02* (2018.01); *A61P 19/06* (2018.01)

(58) Field of Classification Search
USPC .......................................................... 514/406
See application file for complete search history.

(56) References Cited

U.S. PATENT DOCUMENTS

| | | | |
|---|---|---|---|
| 2012/0184582 | A1 | 7/2012 | Song et al. |
| 2014/0357683 | A1 | 12/2014 | Gunawardhana et al. |
| 2016/0039784 | A1 | 2/2016 | Kawana et al. |
| 2021/0338648 | A1 | 11/2021 | Hoegstedt et al. |
| 2024/0000751 | A1 | 1/2024 | Yoo et al. |
| 2024/0293369 | A1 | 9/2024 | Lee et al. |

FOREIGN PATENT DOCUMENTS

| | | | |
|---|---|---|---|
| CN | 105579037 | A | 5/2016 |
| CN | 106008488 | A | 10/2016 |
| EA | 201270520 | A1 | 10/2012 |
| JP | 2013-507355 | A | 3/2013 |
| JP | 2014-510133 | A | 4/2014 |
| JP | 2016-520133 | A | 7/2016 |
| JP | 2019-108356 | A | 7/2019 |
| JP | 2022-511380 | A | 1/2022 |
| JP | 2023-551712 | A | 12/2023 |
| KR | 10-2009-0127870 | A | 12/2009 |
| KR | 10-2009-0128488 | A | 12/2009 |
| KR | 10-2011-0037883 | A | 4/2011 |
| KR | 10-2012-0114174 | A | 10/2012 |
| KR | 10-1424013 | B1 | 8/2014 |
| KR | 10-2015-0138212 | A | 12/2015 |
| KR | 10-1751325 | B1 | 6/2017 |
| RU | 2 477 274 | C2 | 3/2013 |
| WO | 2011/159732 | A1 | 12/2011 |
| WO | 2012/138147 | A2 | 10/2012 |
| WO | 2013/066353 | A1 | 5/2013 |

OTHER PUBLICATIONS

International Search Report dated Sep. 15, 2022 in International Application No. PCT/KR2022/008450.
Khanna, D. et al., "2012 American College of Rheumatology Guidelines for Management of Gout Part I: Systematic Non-pharmacologic and Pharmacologic Therapeutic Approaches to Hyperuricemia," Arthritis Care Res (Hoboken). Oct. 2012, 64(10):1-28.
Li, Q. et al., "Diagnosis and treatment for hyperuricaemia and gout: a protocol for a systematic review of clinical practice guidelines and consensus statements," BMJ Open, 2017, 7:1-6.
Yun, J. et al., "Oxypurinol Directly and Immediately Activates the Drug-Specific T Cells via the Preferential Use of HLA-B*58:01," J Immunol, 2014, 192(7): 2984-2993.
Chen-Xu, M. et al., "Contemporary Prevalence of Gout and Hyperuricemia in the United States and Decadal Trends: The National Health and Nutrition Examination Survey 2007-2016," Arthritis Rheumatol., Jun. 2019, 71(6):1-18.
Bardin, T. et al., "Impact of comorbidities on gout and hyperuricaemia: an update on prevalence and treatment options," Bardin and Richette BMC Medicine, 2017, 15(123):1-11.
Hansildaar, R. et al., "Cardiovascular risk in inflammatory arthritis: rheumatoid arthritis and gout," Lancet Rheumatol, Jan. 2021, 3(1):e58-e70.
Perez-Ruiz, F. et al., "Effect of Urate-Lowering Therapy on the Velocity of Size Reduction of Tophi in Chronic Gout," Arthritis & Rheumatism (Arthritis & Research), Aug. 2002, 47(4):356-360.
Mandell, B. F., et al., "Tophus resolution in patients with chronic refractory gout who have persistent urate-lowering responses to pegloticase," Arthritis Research & Therapy, 2018, 20(286):1-10.
Dalbeth, N. et al., "Lesinurad, a Selective Uric Acid Reabsorption Inhibitor, in Combination With Febuxostat in Patients With Tophaceous Gout: Findings of a Phase III Clinical Trial," Arthritis & Rheumatology, Sep. 2017, 69(9):1903-1913.
Shoji, A. et al., "A Retrospective Study of the Relationship Between Serum Urate Level and Recurrent Attacks of Gouty Arthritis: Evidence for Reduction of Recurrent Gouty Arthritis with Antihyperuricemic Therapy," Arthritis Rheumatism (Arthritis Care & Research), Jun. 2004, 51(3):321-325.
STN Structure Search, Feb. 2023, pp. 1-13.
"History of Changes for Study: NCT03934099 A Study to Assess Efficay and Safety of LC350189 Different Doses in Gout Patients With Hyperuricemia," ClinicalTrials.gov, Apr. 2021, pp. 1-5.
Yoon, S. et al., "Pharmacokinetics, pharmacodynamics, and tolerability of LC350189, a novel xanthine oxidase inhibitor, in healthy subjects," Drug Design, Development and Therapy, Aug. 2015, 9:5033-5049.
Terkeltaub, R., et al., "Phase 2 Study Results from a Randomized, Double-blind, Placebo-controlled, Dose-finding Study to Evaluate Efficacy and Safety of Tigulixostat, a Novel Non-purine Selective Xanthine Oxidase Inhibitor, in Gout Patients with Hyperuricemia," [abstract]. Arthritis Rheumatol., 2021, 73(Suppl. 9), ACR Convergence 2021, Oct. 22, 2021, Abstract No. L05; pp. 1-3.
Office Action dated Apr. 11, 2025 in Chilean Application No. 202303513.
Office Action dated Apr. 22, 2025 in Eurasian Application No. 202393439.
Shiramoto, M., et al., "Verinurad combined with febuxostat in Japanese adults with gout or asymptomatic hyperuricaemia: a phase 2a, open-label study", Pheaumatology, 2018, 57(9): 1-16.
Harrison, R.K., "Phase II and phase III failures: 2013-2015", Nature Reviews Drug Discovery, Dec. 2016, 15(12): 817-818.
Supplementary European Search Report dated Sep. 24, 2024 in European Application No. 22825305.0.
Terkeltaub, R., et al., "Phase 2 Study Results from a Randomized, Double-blind, Placebo-controlled, Dose-finding Study to Evaluate Efficacy and Safety of Tigulixostat, a Novel Non-purine Selective Xanthine Oxidase Inhibitor, in Gout Patients with Hyperuricemia," [abstract]. ACR Convergence 2021, Oct. 22, 2021, Abstract No. L05; pp. 1-3.
Office Action dated Dec. 9, 2024 in Japanese Application No. 2023-574504.
Li, X., et al., "Pharmacological urate-lowering approaches in chronic kidney disease," European Journal of Medicinal Chemistry, Jan. 23, 2019, 166: 186-196, Elsevier.
Pillinger, M.H., et al., "Therapeutic approaches in the treatment of gout," Seminars in Arthritis and Rheumatism, 2020, 50:S24-S30, Elsevier.
Office Action dated Jul. 10, 2024 in Eurasian Application No. 202393439.
Endocrine Society of Chinese Medical Association, "Chinese Expert Consensus on the Treatment of Gout and Hyperuricemia," Chin J Endocrinol Metab, 2013, 29(11):913-920 [Abstract only].
Office Action dated Apr. 21, 2026 in Chinese Application No. 202280034026.

* cited by examiner

PHARMACEUTICAL COMPOSITION COMPRISING 1-(3-CYANO-1-ISOPROPYL-INDOL-5-YL)PYRAZOLE-4-CARBOXYLIC ACID

CROSS-REFERENCE TO RELATED APPLICATIONS

This application is the U.S. national stage application of International Patent Application No. PCT/KR2022/008450, filed Jun. 15, 2022, which claims the benefit under 35 U.S.C. § 119 of Korean Application No. 10-2021-0077709, filed Jun. 15, 2021, the disclosures of each of which are incorporated herein by reference in their entirety.

TECHNICAL FIELD

The present invention relates to a pharmaceutical composition comprising 1-(3-cyano-1-isopropyl-indol-5-yl) pyrazol-4-carboxyl acid.

BACKGROUND ART

Uric acid is produced by xanthine oxidase or xanthine dehydrogenase during purine metabolism. About 70% of blood uric acid is produced by endogenous purine metabolism according to cell turn-over during the cell cycle, and 30% of the uric acid is formed from purines ingested through food, and most of the uric acid is excreted through the kidneys (250 to 750 mg/day).

Accordingly, blood uric acid concentration is maintained at a constant level due to homeostasis between uric acid formation and uric acid excretion, and in this case, when uric acid formation is increased or uric acid excretion is reduced, blood uric acid concentration is increased. Hyperuricemia is generally defined as a blood uric acid concentration of 7.0 mg/dL or more in men and 6.5 mg/dL or more in women. Recently, the number of hyperuricemia patients is increasing due to a high-protein diet, and the like.

When the blood uric acid concentration is increased, the first phenomenon that occurs is the deposition of urate (monosodium urate; MSU) microcrystals in the body. When the blood uric acid concentration is maintained high for a long period of time, and thus the supersaturation state continues, urate microcrystals are formed and deposited in tissues (urate deposits), and urate deposits form gout tophi in tissues or organs such as joints, synoviums, tendons, kidneys, and connective tissues (except the central nervous system). The formed gouty tophi causes acute and chronic inflammation and tissue damage, resulting in multiple systemic damage such as arthritis, urinary calculi, chronic kidney disease (CKD), hypertension, cardiovascular disease, and metabolic syndrome.

The hyperuricemia-related diseases include gout, recurrent gout flare, gouty arthritis, hypertension, cardiovascular disease, coronary heart disease, heart failure, Lesch-Nyhan syndrome, kidney disease, chronic kidney disease, renal calculi, renal failure, diabetic kidney disease, arthritis, urinary calculi, acute and chronic uric acid nephropathy, uric acid calculi, and the like.

A typical disease caused by hyperuricemia is gout. Gout is a type of inflammatory arthritis characterized by unregulated hyperuricemia and an acute gout flare. The continuous supersaturated blood uric acid concentration produces urate crystals and deposits them in the joints and surrounding tissues, resulting in gout. The urate crystals deposited in the joints cause gout flares in acute cases, and result in gout tophi in chronic gout patients with repeated gout flares.

A number of studies have confirmed that a continuous reduction in blood uric acid concentration may reduce the number of gout attacks and gout tophi and may reduce gout tophi. Thus, in the treatment of chronic gout patients, the primary treatment goal is to maintain the blood uric acid concentration in the normal range to inhibit the deposition of urate microcrystals in the tissue and to reduce the number and size of the already formed gout tophi. Accordingly, some reports suggest that the blood uric acid concentration should be lowered to less than 6.0 mg/dL in chronic gout patients and less than 5.0 mg/dL in crystalline gout patients to inhibit further gout attacks and promote the breakdown of urate deposits.

In order to lower the blood uric acid concentration, a xanthine oxidase inhibitor for suppressing the above-mentioned uric acid production is administered, or a uricosuric drug (uric acid reabsorption inhibitor or uricosuric inducer) for increasing the produced uric acid excretion is administered. Alternatively, a uricolytic drug (PEG-uricase) that induces lowering of uric acid by converting uric acid into allantoin and excreting it in the urine is used in a patient who does not respond to the above-mentioned gout treatment agent (PEG-uricase).

As representative xanthine oxidase inhibitors, allopurinol and febuxostat are known. Although allopurinol and febuxostat are used as therapeutic agents to lower the blood uric acid concentration in gout patients due to their low price and dosing convenience (oral administration), only about 40% of the patients in a patient group receiving allopurinol and only 30 to 60% of the patients in a patient group receiving febuxostat had a blood uric acid concentration of less than 6 mg/dL, and the rest of the patient groups still could not reach clinically blood uric acid concentration levels within the normal range.

Thus, for patients who cannot reach the recommended level (less than 6 mg/dL) of blood uric acid concentration despite treatment with conventional xanthine oxidase inhibitors, the American College of Rheumatology recommends combination therapy with a uricosuric inducer.

However, hyperuricemia is usually accompanied by renal dysfunction. In particular, numerous literature results have been reported explaining a direct causal relationship between chronic kidney disease such as CKD and hyperuricemia. In patients with impaired renal function, the excretion of uric acid in the blood may be lowered and the concentration of uric acid in the body may increase, which may lead to hyperuricemia. In addition, increased soluble urate in the body due to hyperuricemia may cause inflammation (pro-inflammatory), thereby lowering renal function. Therefore, there is a need for treating and inhibiting kidney disease by suppressing the excessive production of uric acid in the body. Currently, research on the efficacy of uric acid lowering agents to protect renal function or to slow the progression of renal function impairment is in progress, but it is difficult to secure a dose to show sufficient efficacy. There are limitations that allopurinol is excreted mostly through the kidneys as its main metabolite, oxypurinol, but when renal function is impaired, the exposure of oxypurinol in the body may increase remarkably to cause side effects, and febuxostat should be adjusted to a dose of 40 mg in patients with severe renal dysfunction.

Therefore, there is a need to derive a treatment method and a pharmaceutical composition that may provide reliable results for the effect of regulating blood uric acid concentration without serious side effects in hyperuricemia patients.

PRIOR ART DOCUMENTS

Patent Documents

Korean Patent No. 1751325 (Jun. 21, 2017) titled "novel compounds effective as xanthine oxidase inhibitors, method for preparing the same, and pharmaceutical composition containing the same"

Korean Patent No. 1424013 (Jul. 22, 2014) titled "1-(3-cyano-1-isopropyl-indol-5-yl)pyrazol-4-Carboxylic acid crystalline form and the producing method thereof"

DISCLOSURE

Technical Problem

It is an object of the present invention to provide a pharmaceutical composition for treating or inhibiting a hyperuricemia-related disease, comprising 1-(3-cyano-1-isopropyl-indol-5-yl)pyrazol-4-carboxylic acid or a pharmaceutically acceptable salt thereof at a dosage of 50 to 200 mg/day.

It is another object of the present invention to provide a method of treating or inhibiting a hyperuricemia-related disease in a subject in need thereof, comprising orally administering to the subject a pharmaceutical composition comprising 1-(3-cyano-1-isopropyl-indol-5-yl)pyrazol-4-carboxylic acid or a pharmaceutically acceptable salt thereof at a dosage of 50 to 200 mg/day.

Technical Solution

In order to achieve the above objects, the present invention provides a pharmaceutical composition for treating or inhibiting a hyperuricemia-related disease, comprising 1-(3-cyano-1-isopropyl-indol-5-yl)pyrazol-4-carboxylic acid or a pharmaceutically acceptable salt thereof at a dosage of 50 to 200 mg/day.

The present invention provides a method of treating or inhibiting a hyperuricemia-related disease in a subject in need thereof, comprising orally administering the pharmaceutical composition of the present invention to the subject.

According to one embodiment of the present invention, the dosage of 1-(3-cyano-1-isopropyl-indol-5-yl)pyrazol-4-carboxylic acid or a pharmaceutically acceptable salt thereof is 50 mg/day.

According to one embodiment of the present invention, the dosage of 1-(3-cyano-1-isopropyl-indol-5-yl)pyrazol-4-carboxylic acid or a pharmaceutically acceptable salt thereof is 100 mg/day.

According to one embodiment of the present invention, the dosage of 1-(3-cyano-1-isopropyl-indol-5-yl)pyrazol-4-carboxylic acid or a pharmaceutically acceptable salt thereof is 200 mg/day.

According to one embodiment of the present invention, when the pharmaceutical composition of the present invention is administered daily for 12 weeks to a hyperuricemia patient group having a blood uric acid concentration of 8 to 12 mg/dL, it is possible to lower the blood uric acid concentration to less than 6.0 mg/dL in 55% or more of the patient group.

According to one embodiment of the present invention, when the pharmaceutical composition of the present invention is administered daily for 12 weeks to a hyperuricemia patient group having a blood uric acid concentration of 8 to 12 mg/dL, it is possible to lower the blood uric acid concentration to less than 5.0 mg/dL in 40% or more of the patient group.

According to one embodiment of the present invention, when the pharmaceutical composition of the present invention is administered daily for 12 weeks to a hyperuricemia patient group having a blood uric acid concentration of 8 to 12 mg/dL, it is possible to lower the blood uric acid concentration to less than 4.0 mg/dL in 15% or more of the patient group.

According to one embodiment of the present invention, the hyperuricemia-related disease is gout, recurrent gout flare, gouty arthritis, hypertension, cardiovascular disease, coronary heart disease, heart failure, Lesch-Nyhan syndrome, kidney disease, chronic kidney disease, renal calculi, renal failure, diabetic kidney disease, arthritis, urinary calculi, or a combination thereof.

According to one embodiment of the present invention, the hyperuricemia-related disease is gout.

According to one embodiment of the present invention, the hyperuricemia-related disease is chronic kidney disease.

According to one embodiment of the present invention, the hyperuricemia-related disease is heart failure.

According to one embodiment of the present invention, the pharmaceutical composition of the present invention may further comprise a therapeutic agent for suppressing gout flare.

According to one embodiment of the present invention, the therapeutic agent for suppressing gout flare comprises ibuprofen, probenecid, sulfinpyrazone, colchicine, naproxen, or a combination thereof.

Advantageous Effects

The pharmaceutical composition comprising 1-(3-cyano-1-isopropyl-indol-5-yl)pyrazol-4-carboxylic acid or a pharmaceutically acceptable salt thereof according to the present invention may be usefully used for treating or inhibiting hyperuricemia patients, since it may not only effectively lower the blood uric acid concentration in the hyperuricemia patients, but also maintain the reduced blood uric acid concentration for a long time.

BEST MODE

Figure 1:
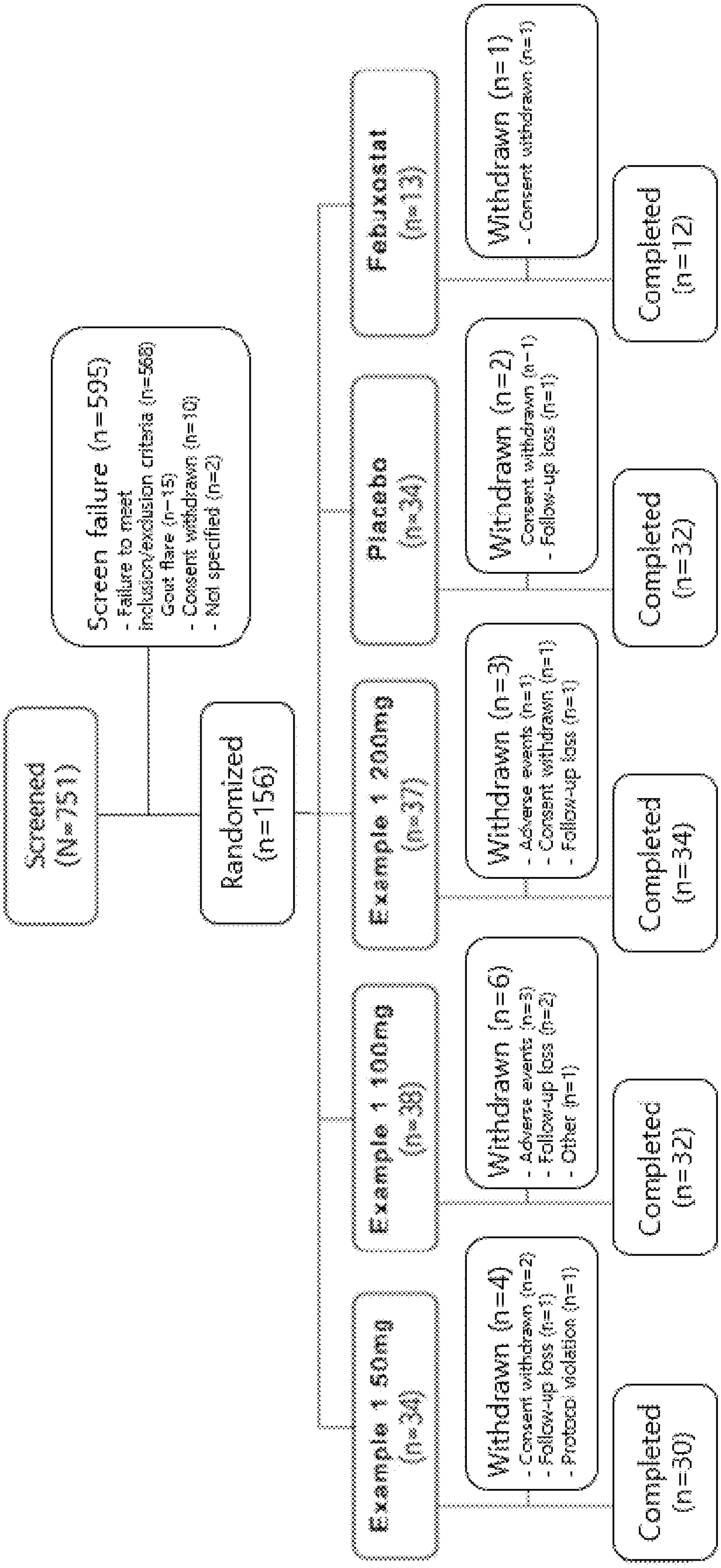
FIG. 1 shows the patient group disposition of the present phase 2 clinical trial.

Hereinafter, the present invention will be described in more detail.

Unless defined otherwise, all technical terms used in the present invention have the same meaning as commonly understood by those skilled in the art in the relevant field of the present invention. In addition, preferred methods or samples are described in the present specification, but similar or equivalent ones are also included in the scope of the present invention. The contents of all publications described as reference documents in the present specification are incorporated in the present specification by reference in their entirety.

It should be understood that although certain aspects herein are described with the term "comprising," other similar aspects described in terms of "consisting of" and/or "consisting essentially of" are also provided.

The terms "patient," "subject," and "individual" are used interchangeably. As used in the present specification, they refer to an individual suffering from a disorder or the like. None of the terms require that "patient," "subject," or "individual" be under the care and/or supervision of a medical professional.

In the present specification, "sUA (serum uric acid)" is used without distinguishing between "blood uric acid" and "serum uric acid."

As used in the present invention, the terms "treat," "treating" and "treatment" and other grammatical equivalents refer to alleviating, attenuating, or ameliorating a disease or condition or one or more symptoms thereof, ameliorating the underlying metabolic cause of the symptom, or inhibiting the disease or condition, e.g., arresting the development of the disease or condition, alleviating the disease or condition, causing inhibition of the disease or condition, alleviating a condition caused by the disease or condition, or stopping the symptoms of the disease or condition.

As used in the present specification, the terms "administer", "administering", "administration", "dose", "dosing", and the like refer to methods that may be used to facilitate delivery of a compound or composition to a desired site of biological action. These methods include, but are not limited to, oral route, intraduodenal route, parenteral injection (including intravenous injection, subcutaneous injection, intraperitoneal injection, intramuscular injection, intravascular injection, or infusion), and topical and rectal administration. A person with ordinary knowledge in the technical field to which the present invention pertains is familiar with administration techniques that may be used with the compounds, compositions, methods, and the like, described in the present specification. In addition, the pharmaceutical composition of the present invention is administered to the subject once a day at about the same time.

As used in the present specification, the terms "effective amount," "therapeutically effective amount," and "pharmaceutically effective amount" refer to a sufficient amount of at least one agent or compound being administered that relieves to some extent one or more of the symptoms of the disease or condition being treated. An "effective amount" for therapeutic use is the amount of a composition comprising the compound as disclosed in the present specification necessary to provide a clinically significant reduction in disease. An appropriate "effective" amount may vary between individuals. An appropriate "effective" amount for any individual may be determined using techniques such as dose escalation studies.

In some embodiments of the present specification, 1-(3-cyano-1-isopropyl-indol-5-yl)pyrazol-4-carboxylic acid or a pharmaceutically acceptable salt thereof, which is an active ingredient for xanthine oxidase inhibition, may be used at a "dosage" of 50 mg/day, 100 mg/day, or 200 mg/day.

As used in the present specification, the term "pharmaceutical composition" refers to a composition comprising at least one pharmaceutically acceptable chemical ingredient, for example, at least one ingredient of excipients such as, but not limited to, carriers, stabilizers, diluents, dispersants, suspending agents and thickeners.

As used in the present specification, the term "pharmaceutically acceptable salt" refers to a salt that retains the biological effectiveness of the free acids and free bases of the specified compound, and that is not biologically or otherwise undesirable. The compounds described in the present specification may have acidic or basic groups, and thus may react with a number of inorganic or organic bases, and inorganic and organic acids, to form pharmaceutically acceptable salts.

The term "pharmaceutically acceptable" means a substance that is acceptable to a patient from a pharmacological/toxicological point of view with respect to composition, formulation, safety, and the like, and a "pharmaceutically acceptable carrier" refers to a medium that does not interfere with the effect of the biological activity of the active ingredient(s) and is nontoxic to a subject upon administration.

As used in the present specification, the terms "co-administration" and "administered in combination with" and equivalents thereof are meant to include administration of two or more active ingredients to a single individual. Each active ingredient may be independently included in one preparation (or formulation), and in this case, may be administered by the same or different routes of administration, at the same or different times. Specific substances that may be co-administered or administered in combination will be described later.

Hyperuricemia is a disease characterized by abnormally high levels of uric acid in the blood (7.0 mg/dL or more in men and 6.5 mg/dL or more in women), and may be asymptomatic in some patients with hyperuricemia, but in many cases is associated with at least one other disease or condition.

In hyperuricemia, urate microcrystals are deposited in tissues while the blood uric acid concentration is maintained high, and the deposited urate microcrystals form tophi. The formed tophi causes acute and chronic inflammation and tissue damage, resulting in multiple systemic damage such as arthritis, urinary calculi, chronic kidney disease (CKD), hypertension, cardiovascular disease, and metabolic syndrome.

As specific hyperuricemia-related diseases, gout, recurrent gout flare, gouty arthritis, hypertension, cardiovascular disease, coronary heart disease, heart failure, Lesch-Nyhan syndrome, Kelley-Seegmiller syndrome, kidney disease, chronic kidney disease, renal calculi, renal failure, diabetic kidney disease, joint inflammation, arthritis, urinary calculi, lead poisoning, hyperparathyroidism, psoriasis, sarcoidosis, hypoxanthine-guanine phosphoribosyltransferase (HPRT) deficiency, and the like are known. In particular, urate microcrystals produced in the body are known to be the direct cause of chronic arthritis, urinary calculi, kidney disease, recurrent acute arthritis, bursitis, gout flare, and the like. Gout is accompanied by obesity, diabetes, hypertension, cardiovascular disease, and the like. In addition, as the blood uric acid concentration increases due to the recent increase in protein-oriented diet, the number of gout patients is also increasing, and thus, the management of blood uric acid concentration is of utmost importance in terms of inhibiting the formation of urate microcrystals.

The dosing group according to one embodiment of the present invention may be a hyperuricemia/gout patient having a blood uric acid concentration of 8 to 12 mg/dL, but is not necessarily limited thereto.

It is known that most of the gout patients have a blood uric acid concentration higher than the normal range, and lowering the blood uric acid concentration relieves gout symptoms, and thus, it is most important to regulate the blood uric acid concentration in gout patients. Thus, in the treatment of chronic gout patients, the primary treatment goal is to maintain the blood uric acid concentration in the normal range.

In order to lower the blood uric acid concentration, as mentioned above, a method of suppressing the uric acid production with a xanthine oxidase inhibitor, or a method of administering a uricosuric drug (uric acid reabsorption inhibitor or uricosuric inducer) to increase the produced uric acid excretion is used.

In the present invention, in order to regulate the blood uric acid concentration in hyperuricemia patients, a xanthine oxidase inhibitor for suppressing the uric acid production was administered. The xanthine oxidase is 1-(3-cyano-1-isopropyl-indol-5-yl)pyrazol-4-carboxylic acid represented by following Formula 1 or a pharmaceutically acceptable salt thereof. The pharmaceutical composition of the present invention comprises the 1-(3-cyano-1-isopropyl-indol-5-yl) pyrazol-4-carboxylic acid or a pharmaceutically acceptable salt thereof as an active ingredient having pharmaceutical efficacy.

[Formula 1]

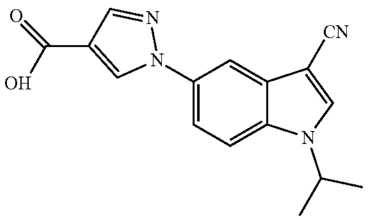

The dosage of 1-(3-cyano-1-isopropyl-indol-5-yl)pyrazol-4-carboxylic acid included in the pharmaceutical composition of the present invention is 50 to 200 mg per day.

Specifically, it may be administered at a dosage of 50 mg/day, 100 mg/day, 150 mg/day, or 200 mg/day.

The pharmaceutical composition of the present invention has the following functions according to the following examples.

When the pharmaceutical composition of the present invention is administered daily for 12 weeks to a hyperuricemia patient group having a blood uric acid concentration of 8 to 12 mg/dL, it is possible to lower the blood uric acid concentration to less than 6.0 mg/dl in 55% or more, 56% or more, 57% or more, 58% or more, 59% or more of the patient group.

When the pharmaceutical composition of the present invention is administered daily for 12 weeks to a hyperuricemia patient group having a blood uric acid concentration of 8 to 12 mg/dL, it is possible to lower the blood uric acid concentration to less than 5.0 mg/dl in 40% or more, 41% or more, 42% or more, 43% or more, 44% or more, 45% or more of the patient group.

When the pharmaceutical composition of the present invention is administered daily for 12 weeks to a hyperuricemia patient group having a blood uric acid concentration of 8 to 12 mg/dL, it is possible to lower the blood uric acid concentration to less than 4.0 mg/dL in 15% or more, 16% or more, 17% or more, 18% or more of the patient group.

The dosage may lower the blood uric acid concentration in hyperuricemia patients, and in particular, when administered at a dosage of 50 mg/day, 100 mg/day or 200 mg/day, most patients (59%, 63%, and 78% of patients in each dosing group) showed a normal blood uric acid concentration of less than 6 mg/dL. In particular, when administered at a dosage of 200 mg/day, a blood uric acid concentration of less than 5 mg/dL was observed in 62% of the patient group, and a blood uric acid concentration of less than 4 mg/dL was observed in 54% of the patient group.

In the febuxostat dosing group, 54% of patients showed a blood uric acid concentration of less than 6 mg/dL, 23% of patients showed a blood uric acid concentration of less than 5 mg/dL, and 0% of patients showed a blood uric acid concentration of less than 4 mg/dL.

In particular, the pharmaceutical composition of the present invention not only lowered the average blood uric acid concentration to 5.5 mg/dL, 4.9 mg/dL, and 3.8 mg within 2 weeks after starting administration in each of the 50 mg/day, 100 mg/day, and 200 mg/day dosing groups, but also maintained the reduced blood uric acid concentration level during the dosing period. However, it can be seen that since febuxostat maintained the blood uric acid concentration level at 5.6 to 5.9 mg/dL, the pharmaceutical composition of the present invention effectively regulates the blood uric acid concentration compared to febuxostat.

The pharmaceutical composition of the present invention can reduce the blood uric acid concentration by 42% or more, 43% or more, 44% or more, 45% or more, 46% or more when administered to a hyperuricemia patient having a blood uric acid concentration of 8 to 12 mg/dL.

The pharmaceutical composition of the present invention may be administered in combination with an active substance having other kinds of pharmaceutical efficacy when administered to a hyperuricemia patient.

In one embodiment of the active substances that may be administered in combination, one or more may be selected from an anti-inflammatory drug for suppressing gout flare, a uricosuric drug, a uricolytic drug, or therapeutic agents for treating other underlying diseases such as diabetes and hypertension.

In one embodiment, the anti-inflammatory drug includes non-steroidal anti-inflammatory drugs (NSAIDs), steroids, colchicine, and the like, and the NSAIDs may be selected from naproxen, indomethacin, sulindac, aceclofenac, ibuprofen, nabumetone, meloxicam, celecoxib, and the like.

The uricosuric drug is a drug with a mechanism of inhibiting urate reabsorption by urate transporter 1 (URAT1), and in one embodiment, may be selected from probenecid, lesinurad, sulfinpyrazone, benzbromarone, high-dose salicylic acid, and the like, and since losartan, amlodipine, atorvastatin, fenofibrate, and the like also indirectly promote uric acid excretion, it may also be selected from these drugs.

According to one embodiment of the present invention, patients were orally administered a tablet comprising a certain dosage of 1-(3-cyano-1-isopropyl-indol-5-yl)pyrazol-4-carboxylic acid in combination with 0.6 mg of colchicine. The purpose of administration in combination with colchicine in the present invention is to inhibit gout flare, which may be caused by urate crystals decomposed in gout tophi when blood uric acid concentration is low.

The pharmaceutical composition of the present invention comprises an effective amount of 1-(3-cyano-1-isopropyl-indol-5-yl)pyrazol-4-carboxylic acid as an active pharmaceutical ingredient (API), and optionally, comprises pharmaceutically acceptable carriers or excipients. In some embodiments, the pharmaceutical composition is useful for treating or inhibiting a condition disclosed in the present specification. In some embodiments, the pharmaceutical composition is for the treatment of a disorder in a human.

The pharmaceutical composition of the present invention may be prepared in a form suitable for oral administration, for example, in formulations such as tablets, troches, aqueous or oily suspensions, dispersible powders or granules, emulsions, hard or soft capsules, syrups, and elixirs. Compositions intended for oral use are optionally prepared according to known methods, and such compositions may contain one or more agents selected from the group consisting of sweeteners, flavoring agents, colorants and preservatives in order to satisfy the preferences of the users.

Tablets contain the active ingredient in admixture with non-toxic pharmaceutically acceptable excipients or carriers suitable for the manufacture of tablets.

Non-limiting examples of suitable pharmaceutically acceptable carriers include solids and/or liquids, for example, ethanol, glycerol, water, and the like. The amount of carrier in the pharmaceutical composition of the present invention may range from about 5 to about 99% by weight based on the total weight of the composition. Non-limiting examples of suitable pharmaceutically acceptable excipients include non-toxic compatible fillers, diluents, binders, disintegrants, buffers, preservatives, wetting agents, extenders, antioxidants, lubricants, flavoring agents, thickeners, colorants, surfactants, emulsifiers, suspending agents, and the like.

In one embodiment, the binder may be selected from the group consisting of, but is not limited to, hydroxypropyl cellulose, hydroxypropyl methylcellulose, hypromellose, polyvinyl acetic acid, povidone, polyvinylpyrrolidone, copovidone, macrogol, sodium lauryl sulfate, light anhydrous silicic acid, synthetic aluminum silicate, silicate derivatives such as calcium silicate or magnesium metasilicate aluminate, phosphates such as calcium hydrogen phosphate, carbonates such as calcium carbonate, pregelatinized starches, gums such as acacia gum, gelatin, cellulose derivatives such as ethyl cellulose, and mixtures thereof.

In one embodiment, the disintegrant may be selected from the group consisting of, but is not limited to, low-substituted hydroxypropyl cellulose, crospovidone, croscarmellose sodium, sodium starch glycolate, F-melt, and combinations thereof.

In one embodiment, the glidant may be selected from the group consisting of, but is not limited to, colloidal silicon dioxide, hydrated silicon dioxide, and combinations thereof. The lubricant may be selected from the group consisting of, but is not limited to, magnesium stearate, silicon dioxide, talc, light anhydrous silicic acid, sodium stearyl fumarate, and combinations thereof.

The present invention further provides kits for use in the methods of prevention or treatment described in the present specification. These kits comprise, in a container, the compound or composition described in the present specification, and optionally, instructions explaining the use of the kit according to the various methods and approaches described in the present specification. In addition, such kits may comprise information, such as scientific references, package insert materials, clinical trial results and/or summaries thereof, that exhibit or establish the activity and/or benefits of the composition and/or describe dosing, administration, side effects, drug interactions, or other information useful to the medical personnel.

The information described in these instructions may be based on the results of various studies, for example, studies using laboratory animals, including in vivo models, and studies based on human clinical trials.

The kits described in the present specification are provided or sold to medical personnels, including doctors, nurses, pharmacists, and the like. In some embodiments, the kit is sold directly to a consumer.

The present invention provides the use of 1-(3-cyano-1-isopropyl-indol-5-yl)pyrazol-4-carboxylic acid or a pharmaceutically acceptable salt thereof for the preparation of a medicament for the prevention or treatment of hyperuricemia.

In addition, the present invention provides a method of treating or inhibiting hyperuricemia by lowering (or regulating) the blood uric acid concentration to less than 6 mg/dL or less than 5 mg/dL, comprising administering the 1-(3-cyano-1-isopropyl-indol-5-yl)pyrazol-4-carboxylic acid or a pharmaceutically acceptable salt thereof to a mammal, including a human, having hyperuricemia symptoms.

In this case, the dosage of 1-(3-cyano-1-isopropyl-indol-5-yl)pyrazol-4-carboxylic acid or a pharmaceutically acceptable salt thereof may be 50 to 200 mg/day, and may be 50 mg/day, 100 mg/day, 150 mg/day, or 200 mg/day.

The hyperuricemia-related disease is selected from gout, recurrent gout flare, gouty arthritis, hypertension, cardiovascular disease, coronary heart disease, heart failure, Lesch-Nyhan syndrome, kidney disease, chronic kidney disease, renal calculi, renal failure, diabetic kidney disease, arthritis, urinary calculi, or a combination thereof.

In addition, in the method of inhibiting or treating hyperuricemia, it may be additionally administered in combination with a therapeutic agent for suppressing gout flare, and the therapeutic agent for suppressing gout flare may include ibuprofen, probenecid, sulfinpyrazone, colchicine, naproxen, or a combination thereof.

Matters mentioned in the pharmaceutical composition, use, and treatment method of the present invention are equally applied as long as they do not contradict each other.

Unless otherwise indicated, all numbers used in the specification and claims, whether recited or not, are to be understood as being modifiable by the term "about" in all instances. It is also to be understood that the precise numbers used in the specification and claims form additional embodiments of the present disclosure. Efforts have been made to ensure the accuracy of the numerical values disclosed in the examples. However, all measured values may inherently include certain error values generated from the standard deviations measured in their respective measurement techniques.

Hereinafter, the present invention will be described in more detail through examples. It will be apparent to those skilled in the art that these examples are only for illustrate the present invention in more detail and the scope of the present invention is not limited to these examples in accordance with the gist of the present invention.

1. Phase 2 Clinical Trial (ClinicalTrials.gov Identifier: NCT03934099)

A phase 2 clinical trial was conducted to analyze the dosage, TEAEs, and the like when the compound of Formula 1 (1-(3-cyano-1-isopropyl-indol-5-yl)pyrazol-4-carboxylic acid; compound of Example 1) is administered to a gout patient group.

Patient Group Selection—Subject Inclusion Criteria

1. Written informed consent (signed and dated) provided voluntarily prior to the start of the study.
2. Male or female aged from 18 to 75
3. History or experience of hyperuricemia and gout in accordance with the criteria of the American College of Rheumatology.
4. Self-reported history of 2 or more gout flare within 12 months prior to screening visit (Visit 1).

5. Blood uric acid (sUA) levels at Visit 1 of 6.0 mg/dL or more in subjects who were receiving urate lower therapy (ULT) with allopurinol, febuxostat, probenecid, or lesinurad; and SUA levels at Visit 1 of 8.0 mg/dL or more and 12.0 mg/dL or less in subjects who had no history of receiving the ULT or were not receiving the ULT at visit 1.
6. SUA levels of 8.0 mg/dL or more and 12.0 mg/dL or less at Visit 3.
7. Body mass index of 42 $kg/m^2$ or less at screening visit (Visit 1).
8. Estimated glomerular filtration rate (eGFR) of 60 mL/min/1.73 $m^2$ or more at screening visit (Visit 1).
9. Subjects of childbearing potential with a negative pregnancy test result at screening visit (Visit 1). Subjects (female subjects of childbearing potential and male subjects with partners of childbearing potential) consented to use adequate methods of contraception to avoid pregnancy during the study period.
10. Able to understand the study procedure and relevant risk, and willing to comply with the visit/protocol schedule.

Patient Group Selection—Subject Exclusion Criteria

1. Presence of secondary hyperuricemia caused by myeloproliferative disorder, organ transplantation, or the like.
2. Experience of any active acute gout flare within 3 weeks prior to screening visit (Visit 1).
3. Aspartate aminotransferase or alanine aminotransferase level exceeds 2 times upper limit of normal (ULN) at screening visit (Visit 1).
4. Creatine kinase level exceeds 2.5 times ULN at screening visit (Visit 1).
5. Presence of previous hypersensitivity to colchicine.
6. Patients who have ever prescribed pegloticase within 3 months prior to screening visit (Visit 1).
7. If a stable dose of drugs (losartan, fibrate, thiazide diuretics, loop diuretics, and acetylsalicylic acid) known to affect sUA levels has not been administered during the past 6 weeks prior to screening visit (Visit 1), acetylsalicylic acid is not allowed to use 325 mg/day or more.
8. Patients who have ever received systemic corticosteroids for 10 or more consecutive days within 1 month prior to screening visit (Visit 1).
9. Presence of need or potential availability of systemic immunosuppressive drugs or immunomodulatory therapies (e.g., azathioprine, 6-mercaptopurine, and cyclosporine)
10. Patients who have received high or moderate doses of cytochrome P450 3A4 inhibitors or P-glycoprotein inhibitors within 14 days prior to screening visit (Visit 1).
11. History of xanthinuria.
12. History of rheumatoid arthritis.
13. Presence of active peptic ulcer disease requiring treatment.
14. Presence of unstable angina, New York Heart Association class III or IV heart failure, myocardial infarction, stroke, deep vein thrombosis, percutaneous coronary intervention (with or without stent), or coronary artery bypass graft within the past 12 months prior to screening visit (Visit 1); current administration of anticoagulants; or the presence of clinically significant electrocardiogram abnormalities in the investigator's opinion at screening visit (Visit 1).
15. Presence of uncontrolled hypertension (systolic blood pressure >160 mmHg or diastolic blood pressure >95 mmHg) at screening visit (Visit 1).
16. History of myositis/myopathy, rhabdomyolysis, Stevens-Johnson syndrome, or toxic epidermal necrolysis.
17. History of malignancy within the past 5 years, except for treated non-melanoma skin cancer, treated cervical dysplasia, or grade 1 cervical cancer in situ with no evidence of recurrence.
18. Persons with known hypersensitivity or allergy to any of the components of the compound of Example 1.
19. Drinking of 14 or more glasses of alcohol for a week (e.g., 1 glass=5 oz [150 mL] of wine, 12 oz [360 mL] of beer, or 1.5 oz [45 mL] of hard liquor).
20. History or suspicion of drug abuse (defined as any illegal drug use) within the past 5 years.
21. Women who are pregnant or nursing.
22. If patients who have ever tested positive for human immunodeficiency virus, active hepatitis B, or HCV infection, Active HCV infection is defined as positive hepatitis C antibody and detectable amount of hepatitis C virus RNA.
23. Previous participation in an interventional clinical study within 3 months or 5 half-lives (whichever is longer) of investigational therapy prior to screening visit (Visit 1).
24. Patients who are suffering from other medical or psychological conditions that investigators and/or medical monitors may cause any excessive risk to the subject or interfere with the subject's ability in complying with or completing protocol requirements.

Selected patients gave written informed consent according to institutional and study procedures. After screening and wash-out processes (days 26 to 33 pre-dose), a total of 156 patients were finally enrolled, and each patient was randomly assigned to 5 groups of 50 mg, 100 mg and 200 mg dosing groups of the compound of Example 1, a placebo group, and a febuxostat group. Patients in each group self-administered 1 tablet of a combination drug (colchicine, 0.6 mg/day) for the prevention of gout flare along with the assigned investigational drug (50 mg, 100 mg and 200 mg doses of the compound of Example 1, placebo, and 40 mg of febuxostat group) orally, once every morning, at about the same time each day, with water, regardless of food.

When ULT is performed using a xanthine oxidase inhibitor compound, since there is a high possibility of gout flare as the tophi dissolves at the end of the bone during the initial treatment period, it was designed to be used in combination with colchicine for the purpose of inhibiting it.

The drug was administered for 84 days by setting the first dosing day of the drug as day 1, and basic tests, blood uric acid concentration and the like were measured at clinic visits on 14 days (week 2), 28 days (week 4), 56 days (week 8), and 84 days (week 12) during the dosing period to determine whether TEAEs occurred. After the end of drug administration, a safety follow-up was performed for an additional 2 weeks (98 days, week 14).

FIG. 1 schematically shows the patient group disposition for the present phase 2 clinical trial.

1-1. Analysis of TEAEs

Among all patient groups participating in the clinical trial, although the administration was stopped for 3 patients due to headache, gout flare in the left ankle, and liver dysfunction in the 100 mg dosing group of Example 1 and for 1 patient due to an increase in hepatic enzyme in the 200 mg dosing group, no significant treatment emergency adverse event (TEAE) was found in the remaining patient groups. In addition, the compound of Example 1 did not show a significant difference in the incidence of TEAEs in all patient groups of 50 mg, 100 mg, and 200 mg, and showed no difference from the placebo group and the febuxostat group in the overall TEAE.

In addition, there were no reports of adverse cardiovascular TEAEs having a causal relationship with the Examples.

However, surprisingly, in the patient groups (50 mg, 100 mg, and 200 mg) receiving the compound of Example 1, 59%, 63%, and 78% of the patients each showed a blood uric acid concentration of less than 6 mg/dL, and 47%, 45%, and 62% of the patients showed a blood uric acid concentration of less than 5 mg/dL (see Table 1). These results demonstrate that the compound of Example 1 exhibits a higher level of blood uric acid reducing effect compared to febuxostat.

TABLE 1

| Dosing group | | Blood uric acid concentration (12 weeks) | | |
|---|---|---|---|---|
| | | <6 mg/dL | <5 mg/dL | <4 mg/dL |
| Example 1 | 50 mg (34 people) | 59% (20/34 people) | 47% (16/34 people) | 18% (6/34 people) |
| | 100 mg (38 people) | 63% (24/38 people) | 45% (17/38 people) | 29% (11/38 people) |
| | 200 mg (37 people) | 78% (29/37 people) | 62% (23/37 people) | 54% (20/37 people) |
| Placebo (34 people) | | 3% (1/34 people) | 3% (1/34 people) | 0% (0/34 people) |
| Febuxostat (13 people) | | 54% (7/13 people) | 23% (3/13 people) | 0% (0/13 people) |

Thus, it can be seen that the compound of Example 1 shows a level of safety similar to that of the placebo group at daily doses of 50 mg, 100 mg, and 200 mg in the treatment of gout.

1-2. Analysis of Changes in Average Blood Uric Acid Concentration During the Dosing Period According to the aforementioned clinic visit schedule, the blood uric acid concentration of the patients in each dosing group was measured on weeks 2, 4, 8 and 12 post-dose. The baseline blood uric acid concentration pre-dose is the blood uric acid concentration measured before dosing on the day of the first dosing. The results are shown in FIG. 2.

Figure 2:
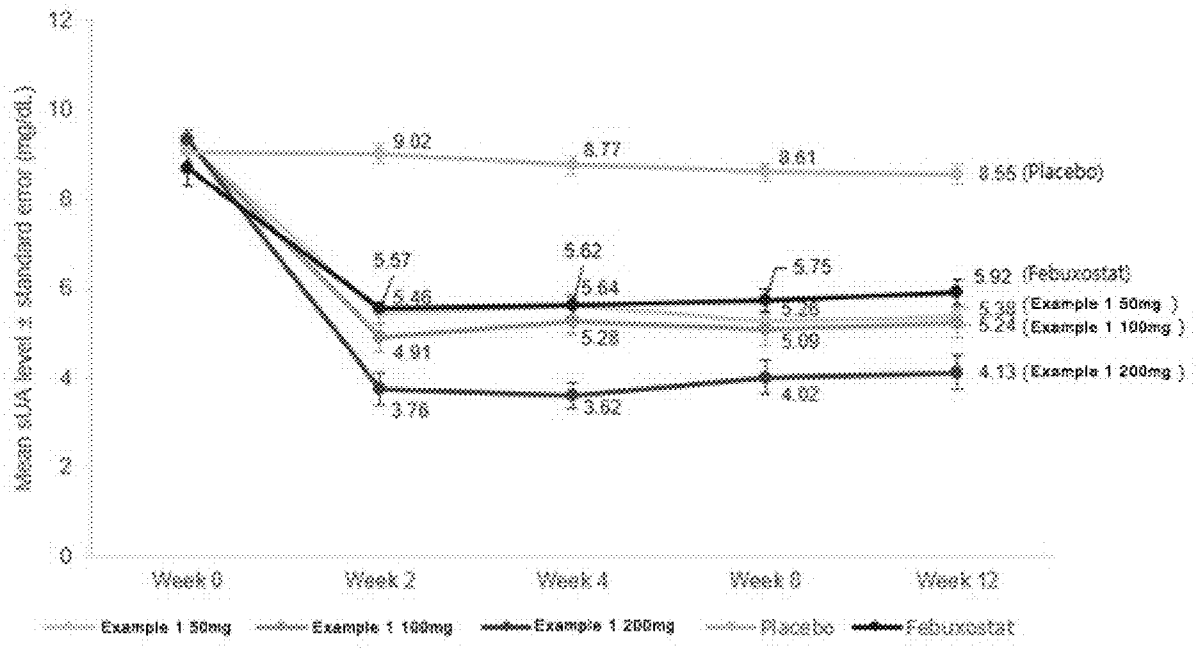
FIG. 2 shows the average blood uric acid concentration according to the dosing period of patients participating in the present phase 2 clinical trial.

According to FIG. 2, in the patient group receiving the compound of Example 1, the blood uric acid concentration was already lowered to the normal range within 2 weeks at the doses of 50 mg, 100 mg, and 200 mg, and kept constant within the normal range (<6.0 mg/dL) during the dosing period. In addition, the compound of Example 1 maintained the blood uric acid concentration similar to or lower than that of febuxostat, and in particular, in the 200 mg dosing patient group, the average blood uric acid concentration was maintained from 3.6 mg/dl to 4.1 mg/dL during the dosing period. Thus, it can be seen that the compound of Example 1 has an equivalent or higher blood uric acid lowering effect when compared to febuxostat, which is a conventional gout treatment.

The European Alliance of Associations for Rheumatology (EULAR)'s 2016 gout management guidelines recommend monitoring blood uric acid concentration levels and maintaining blood uric acid concentration below 6 mg/dL when ULT is performed in gout patients. In addition, it is recommended to keep the blood uric acid concentration at a lower level in patients with severe gout.

As in EULAR 2016, the American College of Rheumatology (ACR) also recommends managing blood uric acid levels at 6 mg/dL in general gout patients (2020 gout management guidelines).

Thus, the number of patients whose blood uric acid concentration was adjusted to less than 6 mg/dL or less than 5 mg/dL in each dosing group was calculated based on the blood uric acid concentration at 12 weeks post-dose.

As a result, only 54% of the patients receiving febuxostat showed a blood uric acid concentration of less than 6 mg/dL, and this result is consistent with the previous result that only 30 to 60% of the patients receiving febuxostat showed a blood uric acid concentration of less than 6 mg/dL (see Table 1).

1-3. Analysis of the Degree of Reduction in Blood Uric Acid Concentration by Patient (Average Maximum Reduction Rate)

Figure 3:
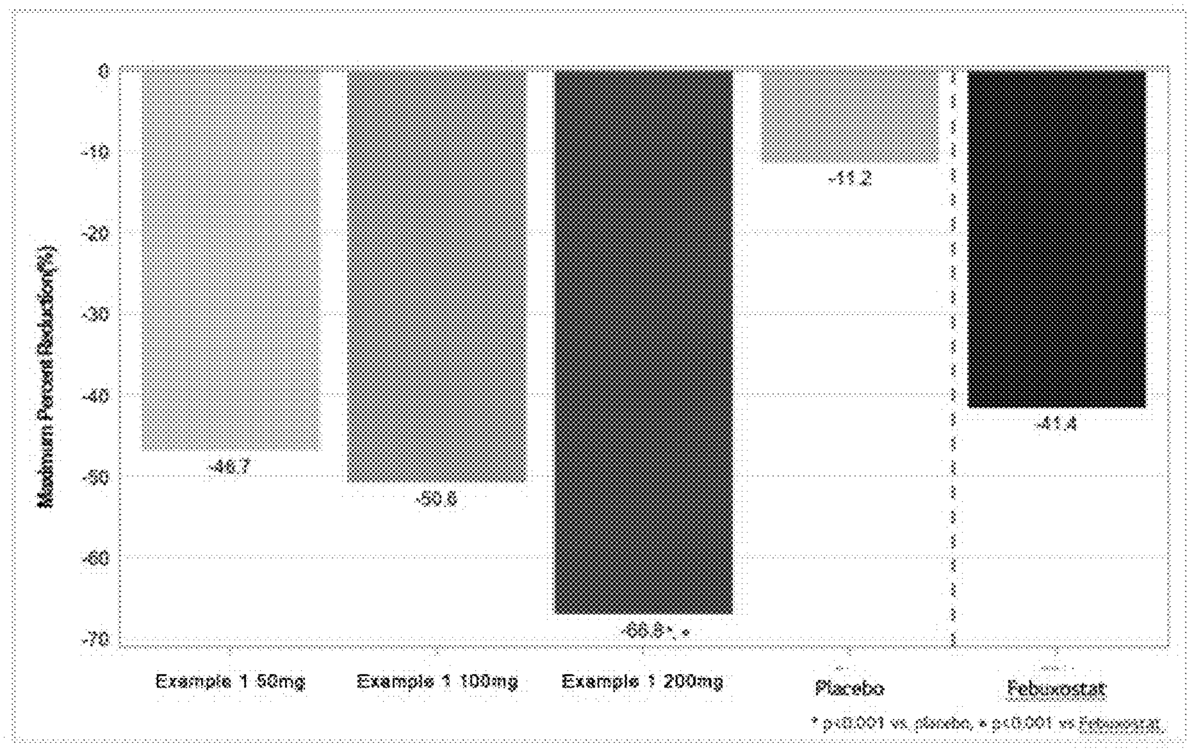
FIG. 3 shows the degree of reduction in the average blood uric acid concentration for each dosing group.

Next, the maximum degree of reduction in blood uric acid concentration was calculated for each dosing group, and the results are shown in FIG. 3. According to FIG. 3, febuxostat showed the degree of reduction in blood uric acid of 41.4%, whereas the compound of Example 1 showed an average maximum degree of reduction in blood uric acid of 46.7%, 50.6%, and 66.8% at 50 mg, 100 mg, and 200 mg, respectively, and thus, it was confirmed that the compound of Example 1 not only had a blood uric acid reducing effect to a higher degree compared to febuxostat, but also had a dose-dependent effect.

The invention claimed is:

1. A pharmaceutical composition for treating a hyperuricemia-related disease of a subject, the pharmaceutical composition comprising:

1-(3-cyano-1-isopropyl-indol-5-yl) pyrazol-4-carboxylic acid or a pharmaceutically acceptable salt thereof; and a therapeutic agent for suppressing gout flare, wherein the therapeutic agent for suppressing gout flare comprises ibuprofen, sulfinpyrazone, colchicine, naproxen, or any combination thereof, and wherein a mass ratio of the therapeutic agent to the 1-(3-cyano-1-isopropyl-indol-5-yl)pyrazol-4-carboxylic acid or a pharmaceutically acceptable salt thereof is in a range of 1.2 mg per 100 mg to 0.3 mg per 100 mg.

2. A method of treating a hyperuricemia-related disease in a subject in need thereof, comprising orally administering to the subject a pharmaceutical composition comprising 1-(3-cyano-1-isopropyl-indol-5-yl)pyrazol-4-carboxylic acid or a pharmaceutically acceptable salt thereof at a dosage of 50, 100, or 200 mg/day, wherein when the pharmaceutical composition is administered daily for 12 weeks to the subject the blood uric acid concentration in the subject is reduced to less than 6.0 mg/dL.

3. The method according to claim 2, wherein the dosage is 50 mg/day.

4. The method according to claim 2, wherein the dosage is 100 mg/day.

5. The method according to claim 2, wherein the dosage is 200 mg/day.

6. The method according to claim 2, wherein when the pharmaceutical composition is administered daily for 12 weeks to the subject, the blood uric acid concentration in the subject is reduced to less than 5.0 mg/dL.

7. The method according to claim 2, wherein when the pharmaceutical composition is administered daily for 12 weeks to the blood uric acid concentration in the subject is reduced to less than 4.0 mg/dL.

8. The method according to claim 2, wherein the hyperuricemia-related disease is gout, recurrent gout flare, gouty arthritis, hypertension, cardiovascular disease, coronary heart disease, heart failure, Lesch-Nyhan syndrome, kidney disease, chronic kidney disease, renal calculi, renal failure, diabetic kidney disease, arthritis, urinary calculi, or any combination thereof.

9. The method according to claim 8, wherein the hyperuricemia-related disease is gout.

10. The method according to claim 8, wherein the hyperuricemia-related disease is chronic kidney disease.

11. The method according to claim 8, wherein the hyperuricemia-related disease is heart failure.

12. The method according to claim 2, wherein the pharmaceutical composition further comprises a therapeutic agent for suppressing gout flare.

13. The method according to claim 12, wherein the therapeutic agent for suppressing gout flare comprises ibuprofen, probenecid, sulfinpyrazone, colchicine, naproxen, or any combination thereof.

14. A method of treating a subject having hyperuricemia, the method comprising:

a) measuring the blood uric acid concentration in a subject; and, for a subject having a blood uric acid concentration of 8.0 to 12.0 mg/dL, b) administering a composition comprising 1-(3-cyano-1-isopropyl-indol-5-yl) pyrazole-4-carboxylic acid or a pharmaceutically acceptable salt thereof to the subject having a blood uric acid concentration of 8.0 to 12.0 mg/dL at an administration dose of 50, 100, or 200 mg/day, wherein the composition is administered orally, and wherein the blood uric acid concentration in the subject is reduced to less than 6.0 mg/dL in two weeks or less than two weeks.

15. The method of claim 14, wherein the blood uric acid concentration in the subject is reduced to less than 5.0 mg/dL.

16. The method of claim 15, wherein the blood uric acid concentration in the subject is reduced to less than 5.0 mg/dL in two weeks or less than two weeks.

17. The method of claim 14, wherein the blood uric acid concentration in the subject is reduced to less than 4.0 mg/dL.

18. The method of claim 17, wherein the blood uric acid concentration in the subject is reduced to less than 4.0 mg/dL in two weeks or less than two weeks.

* * * * *